United States Patent [19]

Merger et al.

[11] 4,192,949

[45] Mar. 11, 1980

[54] PREPARATION OF ARALKYL PHENYL ETHERS AND ALKYL PHENYL ETHERS

[75] Inventors: Franz Merger, Frankenthal; Friedrich Towae, Ludwigshafen, both of Fed. Rep. of Germany; Ludwig Schroff, deceased, late of Ludwigshafen, Fed. Rep. of Germany, by Meinie T. Schroff, heiress-at-law

[73] Assignee: BASF Aktiengesellschaft, Fed. Rep. of Germany

[21] Appl. No.: 915,716

[22] Filed: Jun. 15, 1978

[30] Foreign Application Priority Data

Jun. 28, 1977 [DE] Fed. Rep. of Germany ....... 2729031
Feb. 28, 1978 [DE] Fed. Rep. of Germany ....... 2807762

[51] Int. Cl.² .................. C07C 43/20; C07C 43/22; C07C 43/25; C07C 43/24
[52] U.S. Cl. .................. 560/67; 568/658; 568/656; 568/584; 260/592; 260/600; 260/590 R; 568/652; 568/632; 568/630; 568/651; 568/650; 568/648; 560/71; 560/144; 260/609 D; 260/609 F; 568/640; 568/642; 260/465 F

[58] Field of Search .......... 260/612 R, 612 D, 613 D, 260/592, 600, 590 R, 609 D, 609 F, 465 F; 568/632, 633, 634, 631, 648, 649, 651, 656, 658, 584, 652, 630, 650, 640, 642; 560/67, 71, 144

[56] References Cited

FOREIGN PATENT DOCUMENTS 2160111  6/1972  Fed. Rep. of Germany .
2334736  4/1975  Fed. Rep. of Germany .

OTHER PUBLICATIONS

Einhorn, Berichte, vol. 42, (1909), 2237-2238.
Rodd, Chemistry of Carbon Compounds, vol. I, Part B, (1952), 888.
Ullmanns Encyklopödie der Technischen Chemie, vol. 13, pp. 450-453 & vol. 14, pp. 760-763.
Houben-Weyl, Methoden der Organischen Chemie, vol. 6/3, pp. 11-18, and 54-71.

*Primary Examiner*—Bernard Helfin
*Attorney, Agent, or Firm*—Keil & Witherspoon

[57] ABSTRACT

Phenol ethers are prepared by reacting phenols with dialkyl carbonates in the presence of tertiary amines and/or phosphines. The aralkyl aryl ethers and alkyl aryl ethers obtained are starting materials for the manufacture of dyes, crop protection agents and scents.

10 Claims, No Drawings

PREPARATION OF ARALKYL PHENYL ETHERS AND ALKYL PHENYL ETHERS

The present invention relates to a novel process for the preparation of phenol ethers by reacting a phenol with a dialkyl carbonate in the presence of a tertiary amine and/or phosphine.

Houben-Weyl, Methoden der Organischen Chemie, volume 6/3, pages 54–71, discloses that phenols can be alkylated with alkyl esters of inorganic acids or with chlorocarbonic acid esters. The esters of sulfuric acid and of the hydrogen halides have attained particular importance for this purpose. The reaction is preferably carried out in the presence of an aqueous or alcoholic alkali metal hydroxide solution, sodium carbonate or potassium carbonate. In the case of polyhydric phenols having two hydroxyl groups in the meta-position, eg. in the case of resorcinol, the alkylation must be carried out in an acid medium since otherwise substantial amounts of nuclear alkylation products are formed (loc. cit., pages 59 and 60). However, all these processes suffer from certain disadvantages. For example, in the alkylation with esters of strong inorganic acids (eg. with dimethyl sulfate or methyl iodide) one equivalent of acid is liberated for each alkyl group introduced, and this acid must again be removed by neutralizing. Furthermore, many of these alkylating agents, for example dimethyl sulfate, are extremely toxic. The use of alkalis is a disadvantage particularly in the case of polyhydric phenols, since their sensitivity to alkali leads to substantial losses.

The reaction of alcohols per se (loc. cit., pages 11–18) is also unsatisfactory when carried out industrially, since the use of strong acids, eg. sulfuric acid, causes difficulties in respect of corrosion of parts of the plant, difficulty of removing the catalyst and in some cases sensitivity of other functional groups to hydrolysis.

We have found that aralkyl phenyl ethers and alkyl phenyl ethers of the formula

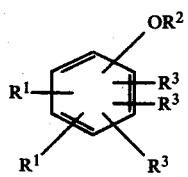   I where the radicals $R^1$ may be identical or different and each is hydrogen, hydroxyl or $-OR^2$, or the two radicals $R^1$ together with two mutually adjoining carbon atoms of the benzene ring may be an aromatic radical, $R^2$ is an araliphatic or aliphatic radical and the radicals $R^3$ may be identical or different and each is an aliphatic, araliphatic or aromatic radical, hydrogen, halogen, cyano, nitro,

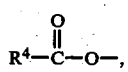

$R^4-S-$ or $R^4-O-$, where $R^4$ is an aliphatic or aromatic radical, may be obtained advantageously when a phenol of the formula

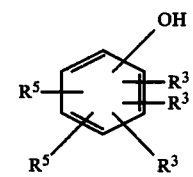   II where $R^3$ has the above meanings and $R^5$ has the meanings of $R^1$ or, if $R^1$ is $-OR^2$, may also be hydroxyl, is reacted with a diaralkyl carbonate or a dialkyl carbonate of the formula

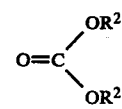   III where the radicals $R^2$ may be identical or different and have the above meanings, in the presence of a tertiary amine and/or of a tertiary phosphine, at above 100° C.

Where phenol and dimethyl carbonate are used, the reaction may be represented by the following equation:

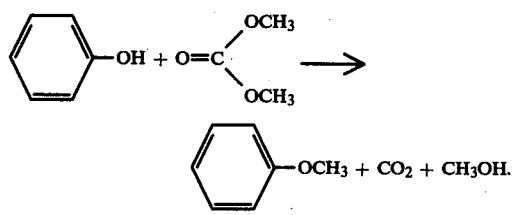

Compared to the conventional processes, the process of the invention gives a large number of phenol ethers more simply and more economically, in good yield and high purity. Involved isolation and neutralization operations are avoided, as are corrosion problems. Apart from the end product, only one mole of alcohol and carbon dioxide, which is nontoxic, are formed; hence, the process of the invention causes less pollution of the environment than do the conventional processes. The alcohol liberated can be reconverted in the conventional manner (see German Laid-Open Application DOS No. 2,334,736) to dialkyl carbonate or diaralkyl carbonate by means of CO and oxygen, without using phosgene $$2 R^2OH + CO + \tfrac{1}{2}O_2 \rightarrow O=C(OR^2)_2 + H_2O$$

All these advantageous aspects of the process of the invention are surprising in view of the prior art. Furthermore, tertiary amines and especially pyridines, which are conventionally used as acylation catalysts, would not have been expected to be active catalysts for the etherification reaction.

The dialkyl carbonates may be prepared in the conventional manner, for example by the processes described in German Laid-Open Application DOS No. 2,160,111 or more advantageously, particularly from the point of view of protection of the environment, by reacting an alcohol with carbon monoxide and oxygen in the presence of a copper catalyst by the method described in German Laid-Open Application DOS No. 2,334,736. The phenol starting materials may contain 2 or 3 hydroxyl groups or preferably one reactive hydroxyl group. Preferred starting materials II and III and, accordingly, preferred end products I are those where the radicals $R^1$ are identical or different and each is hydrogen, hydroxyl, or $-OR^2$, or both radicals $R^1$ together with two mutually adjoining carbon atoms of the benzene ring are a fused phenylene radical, the radicals $R^2$ are identical or different and each is aralkyl of 7 to 12 carbon atoms or especially alkyl of 1 to 7, advantageously of 1 to 4, carbon atoms, the radicals $R^3$ are identical or different and each is phenyl, aralkyl of 7 to 12 carbons or especially alkyl of 1 to 12, advantageously of 1 to 6, carbon atoms, alkenyl of 2 to 12, advantageously of 2 to 6, carbon atoms, or, preferably, a double bond, alkyl of 1 to 12 carbon atoms, advantageously of 1 to 6 carbon atoms, substituted by 2 oxo groups or preferably by one oxo group, hydrogen, bromine, chlorine, cyano, nitro,

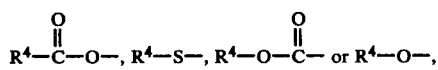

where $R^4$ is alkyl of 1 to 12, advantageously of 1 to 6, carbon atoms or is phenyl, and $R^5$ has the meanings of $R^1$ or, if $R^1$ is $-OR^2$, are hydroxyl. The above radicals may in addition be substituted by groups which are inert under the reaction conditions, eg. alkyl or alkoxy each of 1 to 4 carbon atoms.

The starting material II is reacted with the starting material III in the stoichiometric amount or in excess or in less than equivalent amount, preferably, where II is a monohydroxy compound, with from 1 to 10 moles, especially from 1.2 to 5 moles, of starting material III per mole of starting material II, or if II is a dihydroxy compound and is being converted to a monohydroxymonoether compound I, the reaction is carried out with from 0.1 to 2, especially from 0.2 to 1 mole, of starting material III per mole of starting material II, or if II is a dihydroxy compound and is being converted to a diether I, the reaction is carried out with from 2 to 10, especially from 2 to 5 moles, of starting material III per mole of starting material II, or if II is a trihydroxy compound and is being converted to a dihydroxymonoether compound I, the reaction is carried out with from 0.1 to 2, especially from 0.2 to 1 mole, of starting material III per mole of starting material II, or if II is a trihydroxy compound and is being converted to a monohydroxydiether compound I, the reaction is carried out with from 2.01 to 4, especially from 2.1 to 3 moles, of starting material III per mole of starting material II, or if II is a trihydroxy compound and is being converted to a triether I, the reaction is carried out with from 4.01 to 15, especially from 4.1 to 10 moles, of starting material III per mole of starting material II.

Examples of suitable starting materials II are phenol which is unsubstituted or is monosubstituted, disubstituted, trisubstituted or tetrasubstituted in the 2-position, 3-position, 4-position, 5-position and/or 6-position by identical or different substituents selected from methyl, ethyl, n-propyl, isopropyl, n-butyl, isobutyl, sec.-butyl, tert.-butyl, benzyl, phenyl, cyano, nitro, formyl, acetyl, propionyl, butyryl, bromine, chlorine, β-formylethyl, γ-formylpropyl, δ-formylbutyl, β-acetylethyl, γ-acetylpropyl, δ-acetylbutyl, β-propionylethyl, γ-propionylpropyl, δ-propionylbutyl, methylcarbonyloxy, ethylcarbonyloxy, propylcarbonyloxy, isopropylcarbonyloxy, butylcarbonyloxy, isobutylcarbonyloxy, sec.-butylcarbonyloxy, tert.-butylcarbonyloxy, phenylcarbonyloxy, carbomethoxy, carboethoxy, carbopropoxy, carboisopropoxy, carbobutoxy, carboisobutoxy, carbo-sec.-butoxy, carbo-tert.-butoxy, carbophenoxy, methylthio, ethylthio, propylthio, isopropylthio, butylthio, isobutylthio, sec.-butylthio, tert.-butylthio, phenylthio, methoxy, propoxy, isopropoxy, butoxy, isobutoxy, sec.-butoxy or tert.-butoxy, pyrocatechol, hydroquinone, resorcinol and corresponding pyrocatechols, hydroquinones and resorcinols which are monosubstituted, disubstituted, trisubstituted or tetrasubstituted in the remaining positions by the above groups, α- and β-naphthol and naphthols similarly substituted by the above substituents, pyrogallol, phloroglucinol, 1,3,4-trihydroxy-benzene and similarly substituted trihydroxybenzenes.

Preferred starting materials II are phenol, o-, m- and p-cresol, o-, m- and p-ethylphenol, 2,3-, 2,4-, 2,5-, 2,6-, 3,5- and 3,4-xylenol, o-, m- and p-isopropylphenol, 2,4- and 2,6-dimethylphenol, 2,4,6-trimethylphenol, 2-methyl-5-isopropylphenol, 3-methyl-6-isopropylphenol, o-, m- and p-tert.-butylphenol, octylphenol, nonylphenol, dodecylphenol, 2,6- and 2,4-ditert.-butylphenol, 3-methyl-4,6-ditert.-butylphenol, salicyl alcohol, salicylaldehyde, methyl salicylate, vanillin, methyl gallate, eugenol, isoeugenol, chavibetol, β-(4-hydroxyphenyl)-ethyl methyl ketone, α-naphthol, β-naphthol, 2-, 3- and 4-bromophenol, 2- and 4-nitrophenol, 3-bromo-2,4-dinitrophenol, 4-bromo-2,6-dinitrophenol, 4-acetylphenol, 2- and 4-methylmercaptophenol, pyrocatechol, 4-tert.-butylpyrocatechol, resorcinol, 5-methylresorcinol, 4,6-dimethylresorcinol, hydroquinone, tert.-butylhydroquinone, 2-, 3- and 4-methoxyphenol, 2,4-di-tert.-butyl-6-methylphenol, 2,6-di-tert.-butyl-4-methylphenol, and 2,5- and 2,6-di-tert,-butylhydroquinone.

Suitable starting materials III are dimethyl carbonate, diethyl carbonate, di-n-propyl carbonate, di-n-butyl carbonate, diisobutyl carbonate, dibenzyl carbonate, methyl ethyl carbonate, methyl propyl carbonate and ethyl propyl carbonate; dimethyl carbonate, diethyl carbonate, di-n-propyl carbonate, methyl ethyl carbonate and dibenzyl carbonate are preferred.

The reaction is carried out at above 100° C., in general at from 100° C. to 350° C., preferably from 120° to 300° C., in the case of a monohydroxy compound II advantageously at from 120° to 200° C., especially from 130° to 180° C., in the case of the preparation of a monoether compound I from a dihydroxy compound II or trihydroxy compound II advantageously at from 100° to 170° C., especially from 110° to 150° C., and in the case of the preparation of a diether I or triether I from a dihydroxy compound II or trihydroxy compound II advantageously at from 120° to 200° C., especially from 140° to 180° C., under atmospheric or superatmospheric pressure, preferably under the autogenous vapor pressure of the reaction mixture in an autoclave at the above temperatures, advantageously at from 1 to 200 bars, continuously or batchwise. Advantageously, the reaction mixture at the same time serves as a solution medium or suspension medium. In such cases it is at times advantageous to add an excess of starting material III and/or to add, from the beginning, an additional amount of the alcohol which is formed during the reaction. Solvents which are inert under the reaction conditions may be used, especially when preparing the monohydroxy compounds from the dihydroxy compounds. Examples of suitable solvents are aromatic hydrocarbons, eg. toluene, ethylbenzene, o-, m- and p-xylene, isopropylbenzene, methylnaphthalene, chlorobenzene, o- and m-dichlorobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane and β,β'-dichlorodiethyl ether, aliphatic or cycloaliphatic hydrocarbons, eg. heptane, nonane, gasoline fractions within a boiling range of from 70° to 190° C., cyclohexane, methylcyclohexane, decalin, petroleum ether, hexane, light naphtha, 2,2,4-trimethylpentane, 2,2,3-trimethylpentane, 2,3,3-trimethylpentane and octane, and appropriate mixtures. Advantageously, the solvent is used in an amount of from 100 to 2,000 percent by weight, based on starting material III.

The catalyst used is a tertiary amine, advantageously in an amount of from 0.1 to 10, especially from 1 to 5, mole percent, based on starting material II. Mixtures of the said catalysts may also be used for the reaction. The amine may furthermore be used in the form of a diamine, of the corresponding salts or of a quaternary salt.

Examples of suitable catalysts are trimethylamine, dimethylamino-neopentanol, N,N'-tetramethyldiamino-neopentane, lauryldimethylamine, stearyldimethylamine, pyridine, α-, β- and γ-picoline, quinoline, isoquinoline, quinazoline, quinoxaline, amyldimethylamine, propyldimethylamine, butyldimethylamine, N-methylimidazole, N-methylpyrrole, 2,6- and 2,4-lutidine, triethylenediamine, p-dimethylaminopyridine, N,N-dimethylcyclohexylamine, pyrimidine, acridine, di-(methyl)-, di-(ethyl)-, di-(n-propyl)-, di-(n-butyl)-, di-(pentyl)-, di-(n-hexyl)-, di-(n-heptyl)-, di-(n-octyl)-, di-(n-nonyl)- and di-(n-decyl)-aniline and pyrazolidine, imidazolidine, morpholine, piperidine and pyrrolidine, which last five compounds are monosubstituted at the nitrogen by the above radicals, and also corresponding catalysts in which the molecule contains 2 or 3 of the above radicals which, however, differ from one another, eg. dimethylethylamine. Polymers containing tertiary amino groups, eg. poly-4-vinylpyridine and poly-N-vinylimidazole, may also be used.

Particularly advantageous catalysts are trimethylamine, pyridine, γ-picoline, 4-pyrrolidino-(1')-pyridine and other pyridine derivatives, eg. o-methyl-, m-methyl-, o-ethyl-, m-ethyl-, p-ethyl-, o-propyl-, m-propyl- and p-propyl-pyridine, dimethylamino-neopentanol, N,N'-tetramethyldiamino-neopentane, p-methoxy-, p-ethoxy- and p-propoxy-pyridine, p-dimethylaminopyridine, p-diethylaminopyridine, p-dipropylaminopyridine and poly-4-vinylpyridine.

Another suitable catalyst is a tertiary phosphine which is advantageously used in an amount of from 0.1 to 10, especially from 1 to 5, mole percent, based on starting material II. Mixtures of the said catalysts may also be used for the reaction. The phosphine may also be used in the form of diphosphine. Suitable catalysts are those of the formula

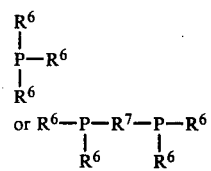

where the radicals $R^6$ may be identical or different and each is an aliphatic or aromatic radical, preferably alkyl of 1 to 6 carbon atoms, alkyl of 2 to 9 carbon atoms substituted by a plurality of cyano groups or preferably by one cyano group, unsubstituted phenyl or phenyl substituted by 1 or 2 alkyl each of 1 to 4 carbon atoms and/or 1 or 2 alkoxy each of 1 to 4 carbon atoms, and $R^7$ is an aliphatic radical, preferably alkylene of 1 to 6 carbon atoms. The above radicals may in addition be substituted by groups which are inert under the reaction conditions, eg. by alkyl or alkoxy each of 1 to 4 carbon atoms or carbalkoxy of 2 to 4 carbon atoms. Examples of phosphine IV and V which are suitable as catalysts are trimethylphosphine, triethylphosphine, tripropylphosphine, triisopropylphosphine, tributylphosphine, triisobutylphosphine, tri-sec.-butylphosphine, triphenylphosphine, P,P-dimethyl-P-neopentylphosphine, P-ethyl-P,P-dimethylphosphine, P-lauryl-P,P-dimethylphosphine, P-stearyl-P,P-dimethylphosphine, P-amyl-P,P-dimethylphosphine, P-propyl-P,P-dimethylphosphine, P,P-butyl-P-dimethylphosphine, P,P-dimethyl-P-phenylphosphine, tri-(pentyl)-phosphine, tri-(n-hexyl)-phosphine, tri-(n-heptyl)-phosphine, tri-(n-octyl)-phosphine, tri-(n-nonyl)-phosphine, tri-(n-decyl)-phosphine, tri-(2-methoxy)-phenylphosphine, tri-o-tolylphosphine, tri-m-tolylphosphine, tri-p-tolylphosphine, tri-o-xylylphosphines, tri-m-xylylphosphines, tri-p-xylylphosphines, the phosphorus preferably being in the m-position to one of the two methyl groups, P,P-bis-(2-cyanoethyl)-P-phenylphosphine, tri-(2-cyanoethyl)-phosphine, tri-(carboethoxymethyl)-phosphine, P-carboethoxymethyl-P,P-diethyl-phosphine, P,P-diethyl-P-(β-carboethoxyethyl)-phosphine, P-carboethoxymethyl-P,P-diphenyl-phosphine, bis-(diphenylphosphino)-alkanes where alkylene is of 1 to 6 carbon atoms, eg. 1,2-bis-(diphenylphosphino)-ethane, bis-(ethylphenylphosphino)-alkanes where alkylene is of 1 to 6 carbon atoms, eg. 1,2-bis-(ethyl-phenyl-phosphino)-ethane and 1,4-bis-(ethyl-phenyl-phosphino)-butane, bis-(dialkylphosphino)-alkanes, where alkylene is of 1 to 6 carbon atoms and alkyl is of 1 to 4 carbon atoms, eg. 1,5-bis-(diethylphosphino)-pentane, P-propyl-P-hexyl-P-nonylphosphine, P-ethyl-P-(2-ethoxyethyl)-P-phenylphosphine, P-isopropyl-P,P-diphenylphosphine and P-butyl-P,P-diphenylphosphine.

The reaction can be carried out as follows: a mixture of the starting materials II and III, of the catalyst and of the solvent, if any, is kept at the reaction temperature for from 1 to 20 hours. The end product is then isolated from the mixture in the conventional manner, for example by fractional distillation.

The aralkyl aryl ethers and alkyl aryl ethers obtainable by the process of the invention are valuable starting materials for the manufacture of dyes, crop protection agents and scents. With regard to their use, reference may be made to the above publications and to Ullmanns Encyklopädie der technischen Chemie, volume 13, pages 450–453, and volume 14, pages 760–763.

In the Examples which follow, parts are by weight.

EXAMPLE 1

19 parts of phenol, 54 parts of dimethyl carbonate and 1 part of p-dimethylaminopyridine are kept at 180° C. for 10 hours. The unconverted dimethyl carbonate is then distilled off and the anisole is isolated from the residue by fractionation. 21.4 parts (98% of theory, based on converted starting material II) of anisole of boiling point 154° C. are obtained. The conversion is virtually quantitative.

EXAMPLE 2

22 parts of hydroquinone, 18 parts of dimethyl carbonate and 1 part of pyrrolidinopyridine in 54 parts of dioxane are kept for 15 hours at 150° C. The mixture is worked up as described in Example 1. 8.0 parts (98% of theory, based on converted starting material II) of hydroquinone monomethyl ether of melting point 57° C. are obtained. The conversion is 33 percent.

EXAMPLE 3

44.4 parts of 2,5-di-tert.-butylhydroquinone, 18 parts of dimethyl carbonate and 1 part of p-dimethylaminopyridine are kept for 20 hours at 200° C. Working up takes place as described in Example 1. 9.5 parts (26% of theory, based on converted starting material II) of 2,5-di-tert.-butylhydroquinone dimethyl ether of boiling point 71°–74° C./0.5 mbar and 22.4 parts (65% of theory) of 2,5-di-tert.-butylhydroquinone monomethyl ether of boiling point 77°–79° C./0.5 mbar are obtained. The conversion is 73 percent.

EXAMPLE 4

22 parts of resorcinol, 18 parts of dimethyl carbonate and 0.5 part of p-dimethylaminopyridine are kept for 10 hours at 180° C. Working up takes place as described in Example 1. 2.3 parts (20% of theory, based on converted starting material II) of resorcinol dimethyl ether of boiling point 214° C. and 9.1 parts (80% of theory) of monomethyl ether of boiling point 245° C. are obtained. The conversion is 46 percent.

EXAMPLE 5

33 parts of eugenol, 50 parts of dimethyl carbonate and 0.5 part of p-dimethylaminopyridine are kept for 20 hours at 200° C. Working up takes place as described in Example 1. 28 parts (99% of theory, based on converted starting material II) of eugenol monomethyl ether of boiling point 69°–70° C./0.13 mbar are obtained. The conversion is 80 percent.

EXAMPLE 6

36 parts of 4-tert.-butylpyrocatechol, 40 parts of dimethyl carbonate and 1 part of p-dimethylaminopyridine are kept for 10 hours at 180° C. Working up takes place as described in Example 1. 18.2 parts (49% of theory, based on converted starting material II) of 4-tert.-butyl-2-hydroxyanisole and 17 parts (46% of theory) of 5-tert.-butyl-2-hydroxyanisole of boiling point 68°–70° C./0.13 mbar are obtained. The conversion is 95 percent.

EXAMPLE 7

33 parts of $\beta$-(4-hydroxyphenyl)-ethyl methyl ketone, 50 parts of dimethyl carbonate and 0.5 part of poly-4-vinylpyridine are kept for 10 hours at 170° C. Working up takes place as described in Example 1. 34.9 parts (98% of theory, based on converted starting material II) of $\beta$-(4-methoxyphenyl)-ethyl methyl ketone of boiling point 94°–95° C./0.26 mbar are obtained. The conversion is virtually quantitative.

EXAMPLES 8 to 19

These are carried out as described in Example 1 (see Table).

TABLE

| Example No. | Parts | Starting material | Parts | End product | Boiling point in °C. | Yield in % of theory | Conversion in % |
|---|---|---|---|---|---|---|---|
| 8 | 23.6 | CH₃–C₆H₄–OH (para) | 17.4 | CH₃–C₆H₄–OCH₃ (para) | 177 | 96 | 68 |
| 9 | 24.5 | 2,6-dimethylphenol | 10.9 | 2,6-dimethylanisole | 182 | 93 | 43 |
| 10 | 24.5 | 3,4-dimethylphenol | 9.1 | 3,4-dimethylanisole | 192 | 96 | 35 |
| 11 | 27.2 | 2,4,6-trimethylphenol | 8.7 | 2,4,6-trimethylanisole | 202 | 100 | 29 |
| 12 | 34.6 | 4-bromophenol | 12.3 | 4-bromoanisole | 223 | 100 | 33 |

TABLE-continued

| Example No. | Parts | Starting material | Parts | End product | Boiling point in °C. | Yield in % of theory | Conversion in % |
|---|---|---|---|---|---|---|---|
| 13 | 27.8 | O₂N—C₆H₄—OH | 10.5 | O₂N—C₆H₄—OCH₃ | 274 | 98 | 35 |
| 14 | 44 | CH₃(CH₂)₈—C₆H₄—OH | 22.7 | CH₃(CH₂)₈—C₆H₄—OCH₃ | 176–180/24 mbar | 78 | 66 |
| 15 | 27.3 | CH₃—C(O)—C₆H₄—OH | 18.3 | CH₃—C(O)—C₆H₄—OCH₃ | 256 | 95 | 64 |
| 16 | 22 | catechol (1,2-(OH)₂C₆H₄) | 6.3 | guaiacol (2-OCH₃-C₆H₄-OH) | 205 | 88 | 29 |
| 17 | 30.5 | HO—C₆H₃(OCH₃)—CHO | 2.3 | CH₃O—C₆H₃(OCH₃)—CHO | 154–155/13 mbar | 12 | 58 |
| 18 | 28.8 | 2-naphthol | 16.5 | 2-methoxynaphthalene | 274 | 93 | 56 |
| 19 | 28.8 | 1-naphthol | 17.1 | 1-methoxynaphthalene | 269 | 89 | 61 |

EXAMPLE 20

The reaction is carried out as described in Example 1, with 18.4 parts of methyl gallate and 80 parts of dimethyl carbonate. 16.5 parts (76% of theory) of methyl 3,4,5-trimethoxybenzoate of boiling point 60°–63° C./0.07 mbar are obtained. The conversion is 96 percent.

EXAMPLE 21

The reaction is carried out as described in Example 1, with 25.2 parts of pyrogallol and 70 parts of dimethyl carbonate. 27.9 parts (83% of theory) of 1,2,3-trimethoxybenzene of boiling point 70°–72° C./0.6 mbar are obtained. The conversion is virtually quantitative.

EXAMPLE 22

The reaction is carried out as described in Example 1, with 22.8 parts of 5-methylresorcinol and 9 parts of dimethyl carbonate. 9 parts (98% of theory) of 5-methylresorcinol monomethyl ether of boiling point 63°–65° C./0.4 mbar are obtained. The conversion is 36 percent.

EXAMPLE 23

19 parts of phenol, 18 parts of dimethyl carbonate and one part of tri-n-butylphosphine in 40 parts of methanol are kept for 10 hours at 180° C. Unconverted dimethyl carbonate and solvent are then distilled off and the anisole is isolated from the residue by fractionation. 14.2 parts (99% of theory, based on converted phenol) of anisole, of boiling point 154° C., are obtained. The conversion is 65 percent.

EXAMPLE 24

33 parts of β-(4-hydroxyphenyl)-ethyl methyl ketone, 54 parts of dimethyl carbonate and one part of triphenylphosphine are kept for 10 hours at 170° C. 23.9 parts (96% of theory, based on converted starting material II) of β-(4-methoxyphenyl)-ethyl methyl ketone of boiling point 94°–95° C./0.26 mbar are obtained. The conversion is 69.5 percent.

EXAMPLE 25

33 parts of eugenol, 50 parts of dimethyl carbonate and 2 parts of tri-n-butylphosphine are kept for 15 hours at 190° C. Working up takes place as described in Example 24. 31 parts (88% of theory, based on converted eugenol) of eugenol methyl ether of boiling point 69°–70° C./0.13 mbar are obtained. The conversion is virtually quantitative.

EXAMPLE 26

22 parts of hydroquinone, 18 parts of dimethyl carbonate and one part of triphenylphosphine are kept for 15 hours at 190° C. Working up takes place as described in Example 23. 3 parts (97% of theory, based on converted hydroquinone) of hydroquinone monomethyl ether of boiling point 57° C. are obtained. The conversion is 12 percent.

We claim:

1. A process for the manufacture of an aralkyl phenyl ether or alkyl phenyl ether of the formula

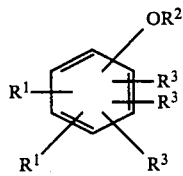

where the radicals $R^1$ are identical or different and each is hydrogen, hydroxyl or —$OR^2$, or the two radicals $R^1$ together with two mutually adjoining carbon atoms of the benzene ring are a fused phenylene radical, the radicals $R^2$ are identical or different and each is aralkyl of 7 to 12 carbon atoms or alkyl of 1 to 7 carbon atoms, the radicals $R^3$ are identical or different and each is phenyl or aralkyl of 7 to 12 carbons or alkyl of 1 to 12 carbon atoms or alkenyl of 2 to 12 carbon atoms, or alkyl of 1 to 12 carbon atoms, substituted by 2 oxo groups or one oxo group, hydrogen, bromine, chlorine, cyano, nitro,

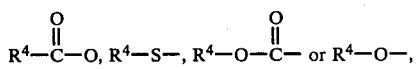

where $R^4$ is alkyl of 1 to 12 carbon atoms or is phenyl, whereby the above radicals may in addition be substituted by alkyl or alkoxy each of 1 to 4 carbon atoms, wherein a phenol of the formula

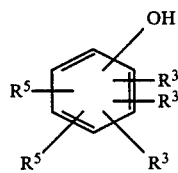

where $R^3$ has the above meanings and $R^5$ has the meanings of $R^1$ or, if $R^1$ is —$OR^2$, may also be hydroxyl, is reacted with a diaralkyl carbonate or a dialkyl carbonate of the formula

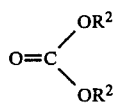

where the radicals $R^2$ are identical or different and have the above meanings, in the presence of a tertiary amine or of a tertiary phosphine or of both at from above 100° C. to 350° C.

2. A process as claimed in claim 1, wherein:
(a) if II is a monohydroxy compound, the reaction is carried out with from 1 to 10 moles of starting material III per mole of starting material II;
(b) or if II is a dihydroxy compound and is being converted to a monohydroxy-monoether compound I, the reaction is carried with from 0.1 to 2 moles of starting material III per mole of starting material II;
(c) or if II is a dihydroxy compound and is being converted to a diether I, the reaction is carried out with from 2 to 10 moles of starting material III per mole of starting material II;
(d) or if II is a trihydroxy compound and is being converted to a dihydroxy-monoether compound I, the reaction is carried out with from 0.1 to 2 moles of starting material III per mole of starting material II;
(e) or if II is a trihydroxy compound and is being converted to a monohydroxy-diether compound I, the reaction is carried out with from 2.01 to 4 moles of starting material III per mole of starting material II;
(f) or if II is a trihydroxy compound and is being converted to a triether I, the reaction is carried with from 4.01 to 15 moles of starting material III per mole of starting material II.

3. A process as claimed in claim 1, wherein the reaction is carried out at from 120° to 300° C.

4. A process as claimed in claim 1, wherein the reaction is carried out, in the case of a monohydroxy compound II, at from 120° to 200° C.

5. A process as claimed in claim 1, wherein the reaction is carried out, in the case of the preparation of a monoether compound I from a dihydroxy compound II or trihydroxy compound II, respectively, at from 100° to 170° C.

6. A process as claimed in claim 1, wherein the reaction is carried out, in the case of the preparation of a diether I or triether I, from a dihydroxy compound II or trihydroxy compound II, at from 120° to 200° C.

7. A process as claimed in claim 1, wherein the reaction is carried out with from 0.1 to 10 mole percent of tertiary amine and/or phosphine, based on starting material II.

8. A process as claimed in claim 1, wherein the reaction is carried out with from 1 to 5 mole percent of tertiary amine and/or phosphine, based on starting material II.

9. A process as claimed in claim 1, wherein the reaction is carried out in the presence of a tertiary amine selected from the group consisting of trimethylamine, pyridine, γ-picoline, 4-pyrrolidino-(1')-pyridine, o-methyl-, m-methyl-, o-ethyl-, m-ethyl-, p-ethyl-, o-propyl-, m-propyl- or p-propylpyridine, dimethylamino-neopentanol, N,N'-tetramethyldiamino-neopentane, p-methoxy-, p-ethoxy- or p-propoxypyridine, p-dimethylaminopyridine, p-diethylaminopyridine, p-dipropylaminopyridine and poly-4-vinylpyridine.

10. A process as claimed in claim 1, wherein the reaction is carried out in the presence of a tertiary phosphine of the formula

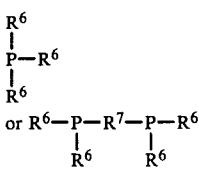

where the radicals $R^6$ are identical or different and each is alkyl of 1 to 6 carbon atoms, alkyl of 2 to 9 carbon atoms substituted by a plurality of cyano groups or preferably by one cyano group, unsubstituted phenyl or phenyl substituted by one or 2 alkyl each of 1 to 4 carbon atoms and/or one or 2 alkoxy each of 1 to 4 carbon atoms, and $R^7$ is alkylene of 1 to 6 carbon atoms, and the above radicals may in addition be substituted by alkyl or alkoxy of 1 to 4 carbon atoms, or carbalkoxy of 2 to 4 carbon atoms.

* * * * *